US010921310B2

(12) United States Patent
Mostafa et al.

(10) Patent No.: US 10,921,310 B2
(45) Date of Patent: Feb. 16, 2021

(54) BIO-FLUID ANALYSIS AND REPORTING SYSTEM AND METHOD

(71) Applicant: Rubriq Corporation, McLean, VA (US)

(72) Inventors: Asghar David Mostafa, McLean, VA (US); Thomas Joseph Brown, Warrenton, VA (US); Joseph Kralowetz, Clarksville, MD (US); Michael Giovannoni, Great Falls, VA (US); Joseph Roesch, Herndon, VA (US); Roland Probst, Rockville, MD (US); Sean Higgins, Gaithersburg, MD (US)

(73) Assignee: Asghar D. Mostafa, McLean, VA (US)

( * ) Notice: Subject to any disclaimer, the term of this patent is extended or adjusted under 35 U.S.C. 154(b) by 272 days.

(21) Appl. No.: 16/046,431

(22) Filed: Jul. 26, 2018

(65) Prior Publication Data

US 2019/0033288 A1 Jan. 31, 2019

Related U.S. Application Data

(60) Provisional application No. 62/537,826, filed on Jul. 27, 2017.

(51) Int. Cl.
*G01N 33/493* (2006.01)
*G01N 33/487* (2006.01)
(Continued)

(52) U.S. Cl.
CPC ......... *G01N 33/493* (2013.01); *A61B 10/007* (2013.01); *G01N 21/77* (2013.01); *G01N 33/48792* (2013.01); *G01N 35/00029* (2013.01); *G01N 35/00871* (2013.01); *G01N 35/1009* (2013.01); *H04Q 9/00* (2013.01); *G01N 21/78* (2013.01); *G01N 21/8483* (2013.01); *G01N 2021/7756* (2013.01); *G01N 2021/7759* (2013.01); *G01N 2035/00881* (2013.01); *H04Q 2209/40* (2013.01)

(58) Field of Classification Search
CPC .......... A61B 2010/0009; A61B 10/007; G01N 33/48; G01N 33/50
See application file for complete search history.

(56) References Cited

U.S. PATENT DOCUMENTS 5,184,359 A * 2/1993 Tsukamura ........ A61B 5/02241
4/314
5,730,149 A * 3/1998 Nakayama ............... G01N 1/12
600/573

(Continued)

FOREIGN PATENT DOCUMENTS

WO 2016066372 A1 5/2016

OTHER PUBLICATIONS

International Search Report and Written Opinion dated Oct. 3, 2018, issued in International Patent Application No. PCT/US2018/044105.

*Primary Examiner* — Thaddeus B Cox
(74) *Attorney, Agent, or Firm* — McGuireWoods LLP

(57) ABSTRACT

A system and method for analyzing bio-fluid constituents and properties in a bio-fluid sample, wherein the system comprises a bio-fluid collection apparatus, a bio-fluid testing/analysis apparatus, and a reporting apparatus.

17 Claims, 11 Drawing Sheets

(51) Int. Cl.

| | |
|---|---|
| *A61B 10/00* | (2006.01) |
| *G01N 35/10* | (2006.01) |
| *G01N 21/77* | (2006.01) |
| *G01N 35/00* | (2006.01) |
| *H04Q 9/00* | (2006.01) |
| G01N 21/84 | (2006.01) |
| G01N 21/78 | (2006.01) |

(56) References Cited

U.S. PATENT DOCUMENTS

| | | | |
|---|---|---|---|
| 2005/0261605 A1* | 11/2005 | Shemer | G01N 21/31 |
| | | | 600/573 |
| 2008/0019871 A1 | 1/2008 | Sakamoto et al. | |
| 2013/0041236 A1 | 2/2013 | Pugia et al. | |
| 2015/0359522 A1* | 12/2015 | Recht | G01N 21/255 |
| | | | 600/573 |
| 2017/0067872 A1* | 3/2017 | Anderson | G01N 33/721 |
| 2017/0284925 A1* | 10/2017 | Spangenberg | G01N 15/14 |
| 2018/0184906 A1* | 7/2018 | Prokopp | A61B 5/4343 |
| 2018/0188231 A1* | 7/2018 | Barakat | A61B 10/007 |
| 2018/0192925 A1* | 7/2018 | Hall | A47K 17/026 |
| 2019/0293636 A1* | 9/2019 | Tsuruoka | G16H 10/40 |
| 2019/0302097 A1* | 10/2019 | Niu | G01N 35/10 |

\* cited by examiner

BIO-FLUID ANALYSIS AND REPORTING SYSTEM AND METHOD

CROSS-REFERENCE TO RELATED APPLICATIONS

This application claims benefit and priority to U.S. Provisional Application No. 62/537,826, filed Jul. 27, 2017, entitled "A BIO-FLUID ANALYSIS AND REPORTING SYSTEM AND METHOD," the disclosure of which is incorporate by reference herein in its entirety.

FIELD OF THE DISCLOSURE

The present disclosure relates to a system and a method that includes bio-fluid collection, analysis and reporting, and, more particularly a system that comprises a bio-fluid collection system, a bio-fluid testing/analysis system, and a results processing and reporting system, as well as a method therefor.

BACKGROUND OF THE DISCLOSURE

Urinalysis is one of the most commonly used methods of diagnosing medical conditions in persons. Urine culture and urine electrolyte testing are also used in diagnosing for certain medical conditions in persons. Over one hundred different tests exist for urine, including chemical-based tests (e.g., existence of proteins, pH levels, glucose, nitrates, ketones, etc.), physical property tests (e.g., color, clarity, smell, specific gravity, etc.), and microscopy analysis (e.g., blood, crystals, etc.). A urine sample's color, smell, and constituents can be helpful in diagnosing medical conditions in the human source such as, e.g., diabetes, cancer, nephritis, muscle damage, jaundice, infection, and many other conditions, too numerous to list here, as known in the medical arts.

Present urinalysis methods tend to be very time-consuming, messy, inconvenient, and costly in both in-patient and out-patient settings. Typically, a person must urinate into a container and physically deliver the container with urine to a healthcare provider or laboratory. After taking appropriate steps to intake, record and track the received container with urine, the healthcare provider/laboratory forwards the urine sample for testing and analysis. The results of the testing and analysis are typically provided to the healthcare provider.

The present urinalysis methods suffer from the following drawbacks, among others: periodic, on demand diagnostic testing takes valuable time in both inpatient and out-patient settings; testing needs to be sent out or done in another area of a medical facility at additional costs; testing can be skewed based on a number of variables such as diet, medication and activities; lab testing gives one time data results and isn't comparable across an individual's baseline; a wide variety of chronic conditions are not regularly tested by the patient; low compliance by patients using conventional methods; and many conditions are not detected early or timely.

The disclosure provides a novel system and method that overcome the disadvantages discussed above, and that meet an unfulfilled need for an efficient, clean, convenient and low-cost solution for collecting bio-fluid, testing/analyzing the collected bio-fluid, and reporting results from the testing/analysis.

SUMMARY OF THE DISCLOSURE

The present disclosure provides an ongoing, easy to use, in-situ bio assessment system and method that users can implement to monitor properties of a bio-fluid such as urine. The in-situ bio assessment system may include a collection system that may be employed with existing toilets.

In one aspect, the bio-fluid assessment system and method may provide test/analysis results in real-time. The bio-fluid assessment system and method may transmit the test/analysis results securely to, for example, a subscriber (e.g., a healthcare provider). For in-situ care (e.g., in-patient care), the testing/analysis can be done on an ongoing and consistent basis. Users can use the bio-fluid assessment system and method to track food, medications and activity. In the case of an unusual sickness or condition, the bio-fluid assessment system may perform testing/analysis prior to the user going to a healthcare provider (e.g., a doctor's office, a hospital, a clinic, a laboratory, or the like). In the case of chronic conditions, subscribers (healthcare providers) can use the bio-fluid assessment system and method to remotely monitor a user's bio-fluid properties and constituents.

According an embodiment of the disclosure, a bio-fluid assessment (BFA) system is provided for analyzing properties and constituents of a bio-fluid such as urine. In one aspect, the BFA system comprises a bio-fluid collection apparatus, an analysis apparatus, and a reporting apparatus.

In one aspect, the bio-fluid collection apparatus may include: a bio-fluid collection apparatus that may include a membrane or substrate that can be placed proximate a toilet bowl for complete collection.

In one aspect, the analysis apparatus may include a chemically activated monitoring substrate; a plurality of testing cells, each of which may comprise a chemical that reacts with a constituent in the urine to give a qualitative test result. The analysis apparatus may include a transmitter or transceiver (transmitter and receiver) that sends analysis data to a user device. The analysis apparatus may include a receiver that receives constituent reference data from, for example, a database. The analysis apparatus may include an analysis processor that compares levels of one or more constituents in the bio-fluid with associated constituent reference data and outputs constituent analysis data based on the constituent levels of the one or more constituents found in the bio-fluid. The analysis apparatus may output the constituent analysis data to the reporting apparatus.

The BFA system may further include a data storage system. The data storage system may comprise one or more databases. The data storage system may comprise a network of databases (database cloud). The data storage system may receive, store, manage, and output constituent reference (or baseline) data, user data, healthcare provider data, and the like. The data storage system may provide constituent reference data for ongoing monitoring by the analysis apparatus. The constituent reference data, user data, healthcare provider data, and/or the like, may be transceived (i.e., transmitted and/or received) securely. Data may be transceived between the data storage system, the analysis apparatus, the reporting apparatus, a user device, a healthcare provider device, and/or the like, over one or more secure communication channels. The data may be encrypted. The data that is transceived may comprise user data, urine test/analysis data, constituent reference data, and the like. The user data may comprise user identification data, diet data, medication data, lifestyle data, vital statistics data, and/or the like. The user identification data may include, for example, name, identification number, social security number, account number, phone number, email address, mailing address, or any other identifier that may associate the user with the bio-fluid. The data may be transceived for immediate use, and include the user's background, diet, medications, and/or the like. The data may be made available in real-time to healthcare providers such as a hospital emergency room (ER), urgent care professional, personal doctor, and the like. The data (including, for example, test results) can be confirmed or used in collaboration with testing/analysis methodologies such as, a blood test, examination data, and/or other testing protocols.

The reporting apparatus may include a transceiver that receives testing/analysis data from the analysis apparatus, and that sends report data to external devices, such as, for example, a user device, a subscriber device, and/or the data storage system.

The BFA system and method disclosed herein may be implemented in, for example, drug testing (e.g., workplace, schools, concerned parents, etc.), pregnancy testing, diabetes testing, sexually transmitted disease (STD) testing, kidney stone testing, eating disorder testing, urinary tract infection (UTI) testing, weight lost monitoring (e.g., ketosis), dehydration (e.g., athletes), nursing home monitoring and in-home elderly care, to name only a few of the many applications of the bio system and/or method.

In one aspect, a bio-fluid analysis system includes a bio-fluid collection apparatus configured to be attached to a toilet and configured to capture bio-fluid from a user, an analysis apparatus to analyze the bio-fluid and to determine one or more constituents in the bio-fluid, and a transmission mechanism to transmit results of an analysis of the captured bio-fluid by the analysis apparatus to a remote computer over a network.

In one aspect, the bio-fluid analysis system may further comprise a compartment in a housing of the bio-fluid collection apparatus to receive a cartridge containing one or more testing substrates for receiving the bio-fluid to be analyzed by the analysis apparatus. Each testing substrate may include a plurality of test cells, each cell for testing for at least one constituent in the bio-fluid. Each testing substrate may include a plurality of test cells each for testing for a level of one or more constituents in the bio-fluid. The bio-fluid collection apparatus may include a processor that is configured to control presenting one or more testing substrates over a portion of the toilet for receiving the bio-fluid to be analyzed by the analysis apparatus. The analysis apparatus may include at least one optical sensor to determine a level of the one or more constituents in the bio-fluid. The at least one optical sensor may comprise a plurality of optical sensors. The bio-fluid analysis system may further comprise a fluid transport device for transporting received bio-fluid for analysis.

In one aspect, the bio-fluid collection apparatus may include a biodegradable test strip having thereon a plurality of test cells, each cell for testing for at least one different constituent in the bio-fluid. The bio-fluid analysis system may further comprise a compartment in a housing of the bio-fluid collection apparatus to receive a cartridge containing one or more testing substrates for receiving the bio-fluid to be analyzed by the analysis apparatus, the cartridge containing a power source or a moving mechanism to move the one or more testing substrates proximate the analysis apparatus. Each of the one or more testing substrates comprises one or more test cells for testing for a level of one or more different constituents in the bio-fluid. In one aspect, the transmission mechanism of the bio-fluid analysis system may communicate results of the analysis to a server over a network for data storage and reporting.

In one aspect, a testing substrate for receiving a bio-fluid to be analyzed by an optical analysis apparatus is provided, the at least one testing substrate may include a plurality of test cells, each cell for testing for a level of one or more different constituents in the bio-fluid, the at least one testing substrate configured to be moved automatically by a mechanical moving mechanism, each cell being optical readable to determine the level of the one or more different constituents. The at least one testing substrate may be configured with a plurality of holes for receiving a moving mechanism therein for moving the at least one testing substrate from a cartridge. The plurality of test cells test for one or more constituents in the bio-fluid may include one or more of: a pH value, a protein, a ketone, a sugar, a nitrite, leukocyte esterase, bilirubin, urobilinogen, red blood cells, white blood cells, calcium, amphetamine, barbiturates, benzodiazepines, buprenorphine, cocaine, cotinine, ecstasy (MDMA), ethyl alcohol, ethyl glucuronide, euphorics, fentanyl, heroin, hydrododone, LSD, marijuana, metabolite, methadone, methamphetamine, methaqualone, an opiate/Opoid, oxycodone, phencyclidine, phenobarbital, propoxyphene, a steroid, testable markers, synthetic cannabinoid, and THC cannabinoid.

In one aspect, a bio-fluid analysis method includes providing a collection apparatus configured to be attached to a toilet for collecting a bio-fluid from a user, analyzing the bio-fluid and to determine one or more constituents in the bio-fluid, and transmitting results of the analyzing to a remote computer over a network.

In one aspect, the bio-fluid analysis method may further comprise loading a cartridge in the collection apparatus, the cartridge containing at least one test substrate configured with a plurality of test cells for testing for one or more constituents in the bio-fluid include one or more of: a pH value, a protein, a ketone, a sugar, a nitrite, leukocyte esterase, bilirubin, urobilinogen, red blood cells, white blood cells, calcium, amphetamine, barbiturates, benzodiazepines, buprenorphine, cocaine, cotinine, ecstasy (MDMA), ethyl alcohol, ethyl glucuronide, euphorics, fentanyl, heroin, hydrododone, LSD, marijuana, metabolite, methadone, methamphetamine, methaqualone, an opiate/Opoid, oxycodone, phencyclidine, phenobarbital, propoxyphene, a steroid, synthetic cannabinoid, and THC cannabinoid. The bio-fluid analysis method may further include analyzing the bio-fluid to determine one or more constituents in the bio-fluid, the analyzing being performed in a housing that houses at least in part, the collection apparatus, the analyzing and collecting being controlled by a common processor.

Additional features, advantages, and embodiments of the disclosure may be set forth or apparent from consideration of the detailed description, drawings and attachment. Moreover, it is to be understood that the foregoing summary of the disclosure and the following detailed description, drawings and attachment are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

Figure 1:
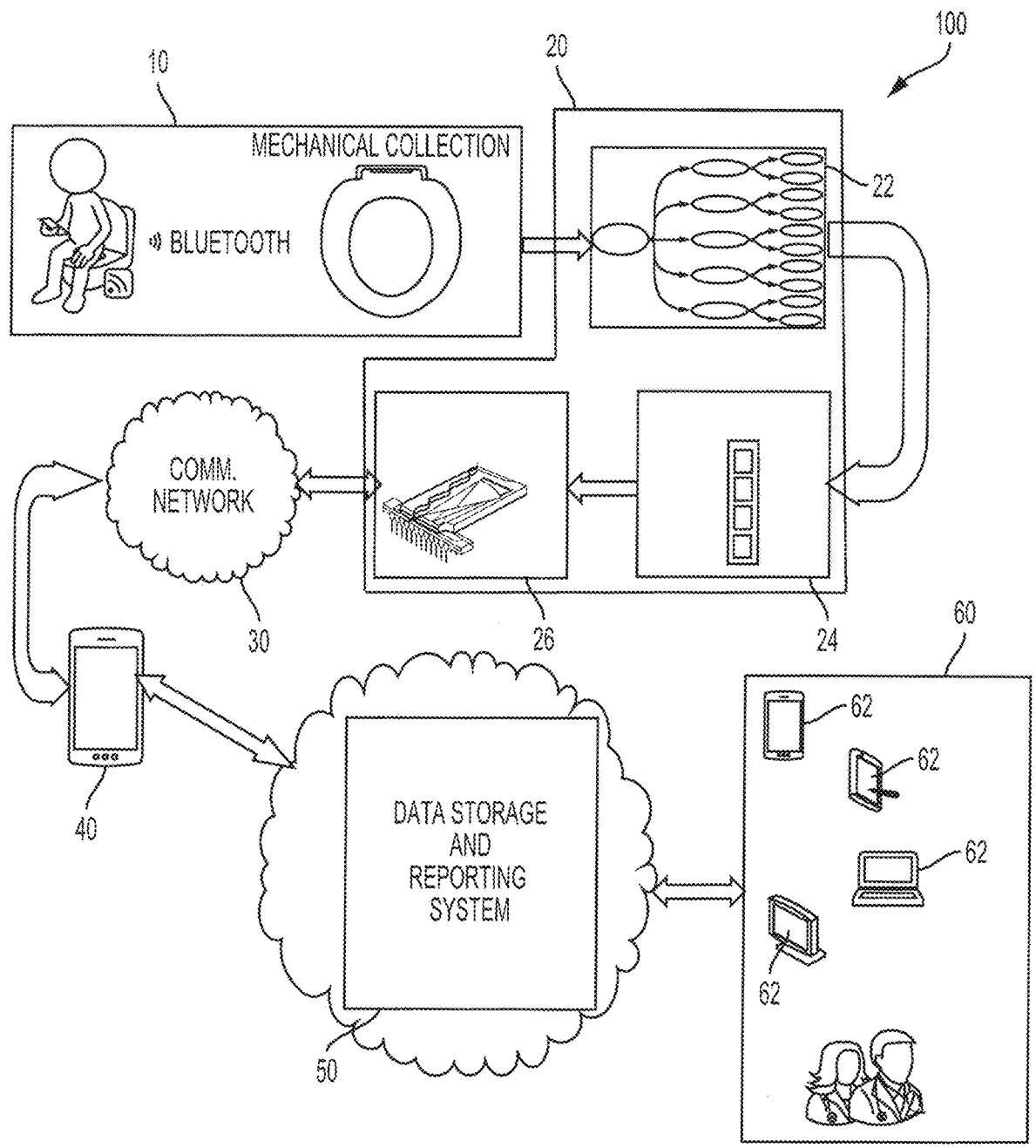
FIG. 1 shows an example of a BFA system, constructed according to the principles of the disclosure.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

FIG. 1 shows an example of a bio-fluid assessment (BFA) system 100 for analyzing properties and constituents in-situ of a bio-fluid such as urine. The BFA system 100 comprises a bio-fluid collection apparatus 10 (shown in more detail below), a bio-fluid analysis apparatus 20, and a reporting apparatus 70 (shown in FIG. 5). The BFA system 100 may comprise a data storage system and reporting system 50, which may include the reporting apparatus 70. The BFA system 100 may comprise a user device 40 and/or a subscriber device 62. The user device 40 and/or the subscriber device 62 may be communicatively coupled in the BFA system 100 via a communication network 30.

The user device 40 may include a phone, a tablet, a computer (e.g., a laptop or desktop), a smart watch, or the like. The user may be any person who may benefit from use of the BFA system 100.

The subscriber device 62 may include a phone, a tablet, a computer (e.g., a laptop, desktop, or any portable device), a smart watch, or the like. The subscriber device 62 may be used by a subscriber 60, such as, for example, healthcare provider (e.g., a medical professional, a medical office, a clinic, a hospital, an urgent care provider, an ambulance, or the like), an employer, an educational facility, a school, or any other person or entity that may benefit from implementation of the BFA system and/or method.

The bio-fluid may include urine. The bio-fluid collection apparatus 10 (see, FIG. 2B) may comprise a physical device that is configured to receive a bio-fluid from a user (male or female) while sitting on, or standing over a toilet. The bio-fluid collection apparatus 10 may include a membrane 325 (FIG. 2C) that facilitates collection.

The analysis apparatus 20 may be located proximate to, or combined with the bio-fluid collection apparatus 10. The analysis apparatus 20 may include a sample channeling (e.g., microfluidics) device 22, a testing device 24, which may be cartridge-based, and an analytic device 26. The sample channeling device 22 may be configured to receive a bio-fluid from the bio-fluid collection apparatus 10 and separate the bio-fluid into a plurality of channels, which may be further separated into sub-channels. The sample channeling device 22 may receive a high volume of fluid and output a low volume of fluid to the testing device 24.

The testing device 24 may include a testing substrate, which may be cartridge based for easy replacement. The testing device 24 may include one or more test cells, each of which may be adapted to detect a unique constituent or property of the bio-fluid, and the concentration or level of the constituent or property. The constituent may include, for example, glucose, ketone bodies, bilirubin, urobilinogen, creatinine, urea, uric acid, catecholamine, dopamine, cortisol, phenylalanine, nitrite, sodium, potassium, urinary calcium, phosphate, protein, human chronic gonadoptropin (hCG), red blood cells, RBC casts, white blood cells, hemoglobin, bacteria, viruses, etc. The property may include, for example, specific gravity, osmolality, pH, color, clarity, etc.

The testing device 24 may include a testing substrate 325 (FIG. 2C) configured with include one or more test cells for detecting one or more conditions such as a unique constituent or property of the bio-fluid, including any one or more of, in any combination shown in TABLE 1.

TABLE 1

| (Sections A-F) |
|---|
| A. Rapid Urine Test attributes |
| pH value |
| Protein (see below) |
| Ketones - Sugar (glucose, not usually found in urine) |
| Nitrites |
| Leukocyte esterase |
| Bilirubin |
| Urobilinogen |
| Red blood cells |
| White blood cells |
| Calcium |
| B. Drugs |
| Amphetamine |
| Barbiturates |
| Benzodiazepines |
| Testable markers |
| Buprenorphine |
| Cocaine |

TABLE 1-continued (Sections A-F)

Cotinine
Ecstasy (MDMA) (3,4-Methylenedioxymethamphetamine)
Ethyl Alcohol
Ethyl Glucuronides
Euphorics
Fentanyl
Heroin
Hydrododone
LSD (Lysergic acid diethylamide)
Marijuana
Metabolite
Methadone
Methamphetamine
Methaqualone
Opiates/Opoids
Oxycodone
Phencyclidine
Phenobarbital
Propoxyphene
Steroids
Synthetic Cannabinoids
THC cannabinoids (phytocannabinoid tetrahydrocannabinol)
C. Prescription testing (compliance with medications)

Measurement of the particular drug, a metabolite or a testable marker
D. Protein in urine, could be a sign of Amyloidosis
Antibody-mediated rejection
Cell-mediated rejection
Chronic kidney disease
Diabetes
Endocarditis
Endocarditis
Fanconi syndrome
Focal segmental glomerulosclerosis
Glomerulonephritis
Heart disease
Heart failure
Hepatitis
High blood pressure (hypertension)
HIV
Hodgkin's lymphoma (Hodgkin's disease)
Hypertensive nephrosclerosis
IgA nephropathy (Berger's disease)
Interstitial nephritis
Kidney infection (pyelonephritis)
Lupus
Lymphoma
Malaria
Multiple myeloma
Nephrotic syndrome
Orthostatic proteinuria
Preeclampsia
Rheumatoid arthritis
Sarcoidosis
Sickle cell anemia
*Streptococcus*
Syphilis
Systemic lupus erythematosus
Uric acid nephropathy
Urinary Tract Inflammation
Uroepithelial tumors
Creutzfeldt-Jakob disease
E. Infectious Disease AKI (Acute Kidney Injury)
CKD (Chronic Kidney Disease)
Diabetic Nephropathy (ESRD)
Rapid kidney function decline (RKFD)
TB in HIV patients
Mosquito-borne diseases
Epstein Barr virus (EBV)
Sexually transmitted infections (STI)
Hepatitis
Tuberculosis (TB)
Malaria
Dengue TABLE 1-continued (Sections A-F)

Influenza A and B
HIV
Chlamydia
Legionnaires' disease
Urinary Tract Infection (UTI)
Cryptococcosis in HIV Patients
F. Pregnancy - presence of human chorionic gonadotrophin (hCG)
hCG (human chorionic gonadotropin) - low levels possible miscarriage
blighted ovum
eptopic pregnancy
hCG - high levels molar pregnancy
multiple pregnancies
Other potential issues Preeclampsia
Seminoma
Choriocarcinoma
Germ cell tumors
Hydatidiform mole formation
Teratoma with elements of choriocarcinoma
Islet cell tumor The analytic device 26 may include, e.g., a micro-spectrometer. The analytic device 26 may include a bio-fluid analyzer 200 (shown in FIG. 2), which includes a processor 210 and a transceiver 282 that may initiate testing/analysis after receiving an instruction signal from a user device 40 via the communication network 30. The instruction signal may be received over a communication link by any known communication protocol (e.g., BlueTooth, WiFi, cellular, or any other wireless connection, etc.).

According to an embodiment of the disclosure, the analysis apparatus 20 may include one or more fluid analytics sensor 316 (FIG. 2C) which may be a fluid analyzer integrated circuit (e.g., a fluid analysis chip), or any other device that can detect proteins, compounds, chemicals, etc. ("constituents") in a fluid sample, as well as the levels or concentrations of the same. The fluid analytics sensor 316 may be connected to the processor 210 for control. In the example of the device that includes a test substrate 325, which may be a printed test strip, the test strip may include a plurality of colors, each of which may be associated with a particular element. The intensity of the color(s) may be related to the concentration of the identified element. The fluid analytics sensor 316 may comprise an optical spectrometer that measures the colors and intensities related to the concentration of the identified element.

Figure 2A:
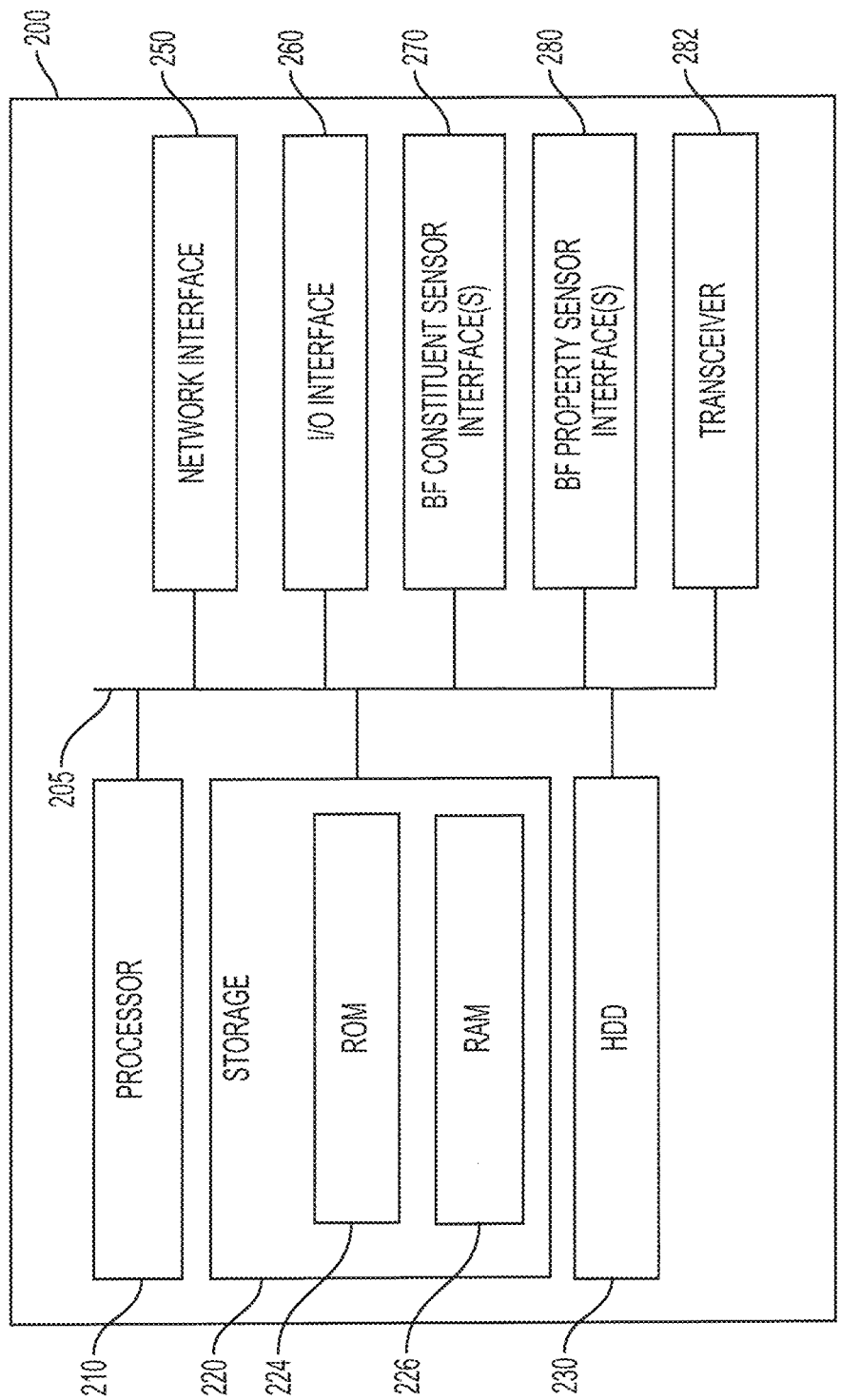
FIG. 2A shows an example of a bio-fluid analyzer that may be included in the BFA system of FIG. 1.

FIG. 2A shows an example of a bio-fluid (BF) analyzer 200 that may be included in the analysis apparatus 20. The BF analyzer 200 is configured to implement the various aspects of the analysis apparatus 20. The BF analyzer 200 includes a processor 210, a system storage 220, and a system bus 205. The BF analyzer 200 includes a bio-fluid (BF) constituent sensor interface 270/or a BF property sensor interface 280, coupled to the fluid analytics sensor 316 (FIG. 2C). The system bus 205 couples the system components including, but not limited to, the system storage 220, the BF constituent sensor interface 270 and/or the BF property sensor interface 280 to the processor 210. The processor 210 can be any of various commercially available processors. Dual microprocessors and other multi-processor architectures may also be employed as the processor 210. The processor 210 may control the operational functions of the analysis apparatus 20 including the fluid analytics sensor 316 and motion of the substrate 325.

The system bus 205 can be any of several types of bus structures that may further interconnect to a memory bus (with or without a memory controller), a peripheral bus, and a local bus using any of a variety of commercially available bus architectures. The system storage 220 may include a read only memory (ROM) 224 and random access memory (RAM) 226. A basic input/output system (BIOS) may be stored in the ROM 224, which may include a non-volatile memory, such as, for example, ROM, EPROM, EEPROM, or the like. The BIOS contains the basic routines that help to transfer information between elements within the computer 300, such as during start-up. The RAM 226 may include a high-speed RAM such as static RAM for caching data.

The BF analyzer 200 may include an internal hard disk drive (HDD) 230, such as, for example, an enhanced integrated drive electronics (EIDE) drive, a serial advanced technology attachments (SATA) drive, or the like. The HDD 230 may be configured for external use in a suitable chassis (not shown). The HDD 230 can be connected to the system bus 205 by a hard disk drive interface (not shown). The hard disk drive interface (not shown) may include a Universal Serial Bus (USB) (not shown), an IEEE 1394 interface (not shown), and the like, for external applications.

The HDD 230 and its associated computer-readable media may provide nonvolatile storage of data, data structures, computer-executable instructions, and the like. The HDD 230 may accommodate the storage of any data in a suitable digital format.

Computer instructions for carrying out the method disclosed herein can be stored in the HDD 230 and/or RAM 226, including an operating system (not shown), one or more application programs (not shown), other program modules (not shown), and program data (not shown). Any (or all) of the operating system, application programs, program modules, and program data may be cached in the RAM 226.

The BF analyzer 200 may include a network interface 250 and an input/output (I/O) interface 260. The BF analyzer 200 may receive instruction and data signals via the I/O interface 260, which may be communicatively coupled to one or more input/output devices, including, for example, a keyboard (not shown), a mouse (not shown), a pointer (not shown), a microphone (not shown), a speaker (not shown), a display (not shown), and/or the like. The received command and data may be forward to the processor 310 from the I/O interface 360 via the bus 302. The BF analyzer 200 may communicate (transmit/receive) instruction and data signal via internal transceiver 282 with the user device 40 (shown in FIG. 1), the data storage and reporting system 50 (shown in FIGS. 1 and 5), and/or the subscriber device 62 (shown in FIG. 1).

The BF analyzer 200 may be coupled to a display device and/or a sound reproduction device, such as, for example, a speaker or an interactive voice response (IVR) device. The display device may be connected to the system bus 205 via the I/O interface 260. The display device may be connected to a video driver via the system bus 205. The sound reproduction device may be connected to the system bus 205 via the I/O interface 260. The sound reproduction device may be connected to an audio driver via the system bus 205.

The network interface 250 may be connected to the network 30 (shown in FIG. 1). The network interface 250 may include a wired or a wireless communication network interface (not shown) and/or a modem (not shown). When used in a local area network (LAN), the BF analyzer 200 may be connected to the LAN network through the wired and/or wireless communication network interface; and, when used in a wide area network (WAN), the BF analyzer 200 may be connected to the WAN network through the modem. The modem (not shown) can be internal or external and wired or wireless. The modem may be connected to the system bus 205 via, for example, a serial port interface (not shown).

The BF constituent sensor interface 270 is adapted to communicate instruction and data signals between the processor 210 and one or more BF constituent sensors (described more fully below), each of which may be adapted to sense a particular BF constituent, and the concentration or level of the particular BF constituent.

The BF property sensor interface 280 is adapted to communicate instruction and data signals between the processor 210 and one or more BF property sensors, each of which may be adapted to sense a particular BF property, and the value or level of the particular BF property.

Figure 2B:
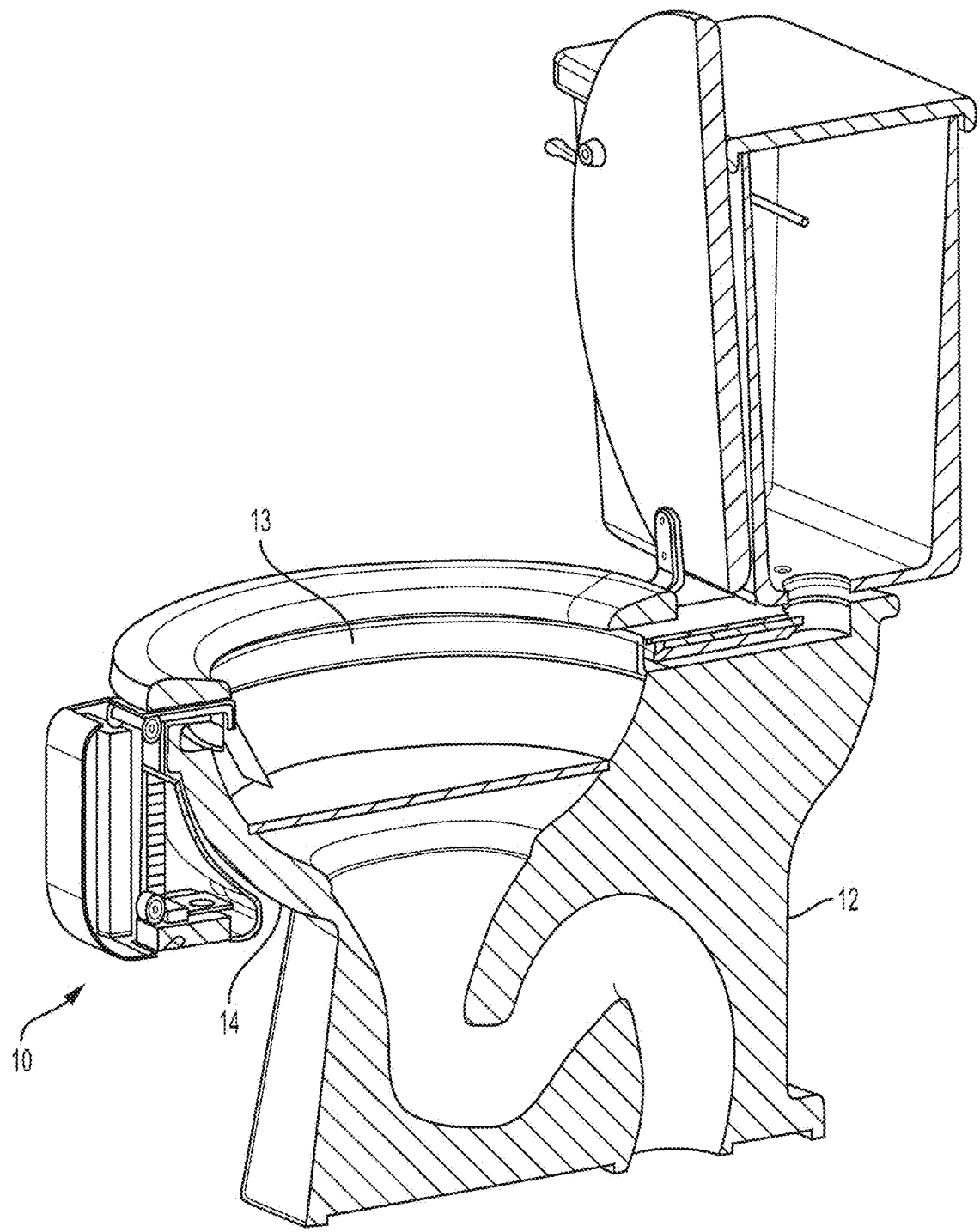
FIG. 2B is an embodiment of a bio-fluid collection apparatus installed on a toilet, according to principles of the disclosure.
Figure 2C:
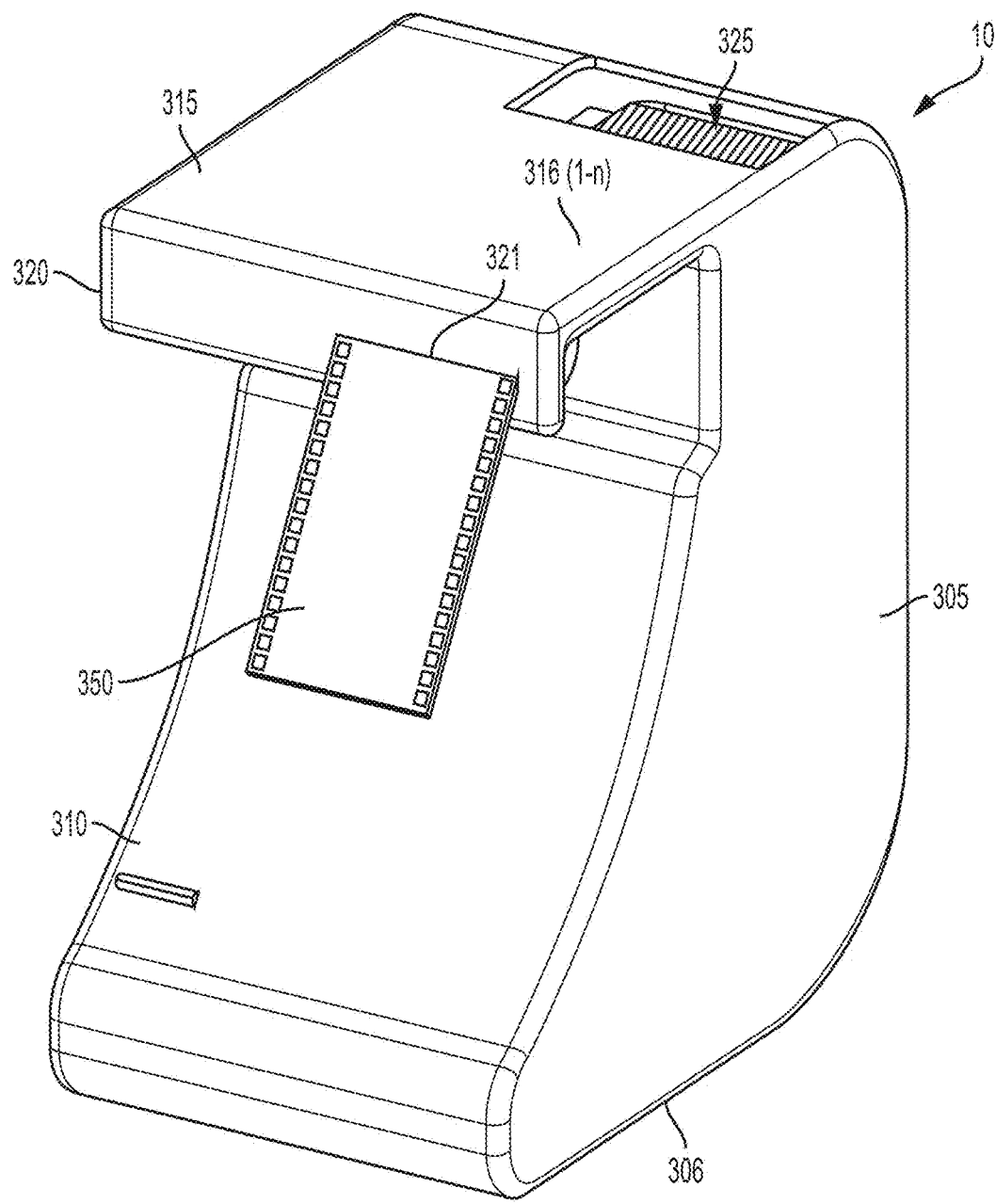
FIG. 2C is an embodiment of a bio-fluid collection apparatus 10, according to principles of the disclosure.

FIG. 2B is an embodiment of a bio-fluid collection apparatus 10 installed on a toilet, according to principles of the disclosure. The toilet 12 may include a contour 14 in the outer surface of the toilet bowl and a rim 13 to which the bio-fluid collection apparatus 10 may be installed. The bio-fluid collection apparatus 10 is oriented so that a user does not need to touch the testing substrate that captures the bio-fluid from a user, which is automatically handled and discharged after use into the toilet 12. In an embodiment, the apparatus 10 may be a part of the toilet or integral to the toilet seat.

FIG. 2C is an embodiment of a bio-fluid collection apparatus 10, according to principles of the disclosure. The bio-fluid collection apparatus 10 may include one or more of the components 22, 24 and 26 of the bio-fluid analyzer 200 of FIG. 1. The bio-fluid collection apparatus 10 may comprise a housing including two opposing sides 305, an opposing front and rear sides 310, and a top side 315 and an opposing bottom side 306. The top side 315 may include a portion that forms a lip 320 for attaching to a toilet 12 (FIG. 2B). The front side 310 may be configured with a concave contour to permit the bio-fluid collection apparatus 10 to be installed and hung on a toilet 12 using lip 320 to connect with a rim 13 of a toilet 12, the concave contour aligning at least to a degree with a corresponding contour 14 of an outer surface of a toilet bowl 12.

The bio-fluid collection apparatus 10 may comprise an opening 325 on the top side 315 to receive a cartridge 345 (FIG. 2E) therethrough of one or more testing substrates 350, which may be the testing device 24 of FIG. 1. The bio-fluid collection apparatus 10 may comprise one or more one or more BF constituent sensors 316 located to optically read results of bio-fluid collected from a user using the one or more testing substrates 350.

Figure 2D:
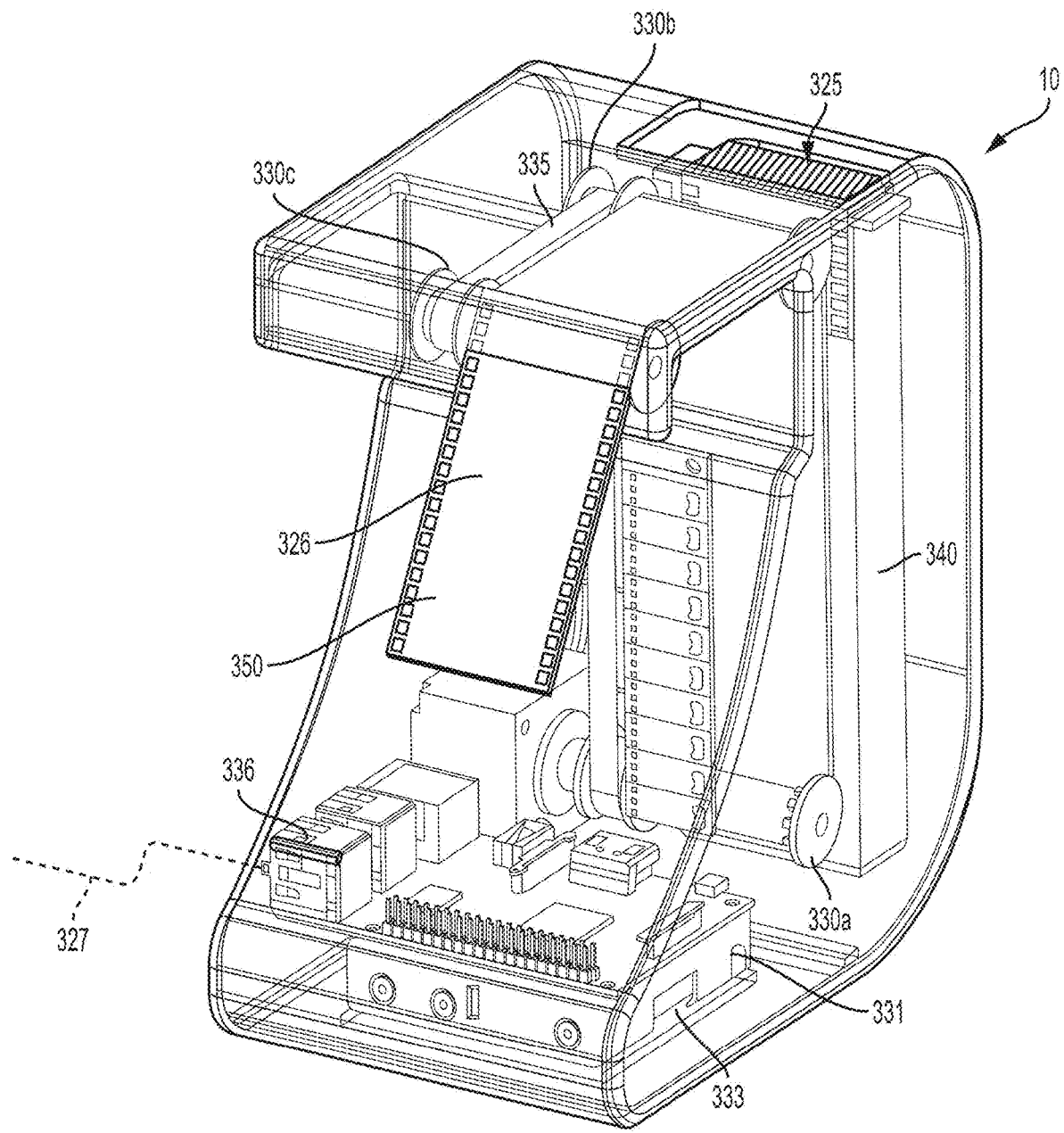
FIG. 2D is an illustration of the bio-fluid collection apparatus of FIG. 2C.

FIG. 2D is an illustration of the bio-fluid collection apparatus of FIG. 2C. The bio-fluid collection apparatus 10 may include a circuit board 333 for interconnecting devices shown in relation to FIG. 2A, the one or more BF constituent sensors 316 and for controlling operation of the moving mechanisms such as pulleys 335 and gears 330a-330c. A battery 331 that might be rechargeable, can be used to power the bio-fluid collection apparatus 10. In some embodiments, the bio-fluid collection apparatus 10 may be connected to an external power source 327.

A compartment 340 is configured to receive therein a cartridge 345 which may have one or more testing substrates 350. The compartment 340 may be a part of the bio-fluid collection apparatus 10 and configured to permit the one or more testing substrates 350 to be moved proximate the one or more BF constituent sensors 316.

During use by a user, a user input mechanism such as button 336 may be used to initiate the bio-fluid collection process. Once the process is initiated by a user, one of the testing substrates 350, which may have more than one testing cells 326 thereon, may be automatically moved from the replaceable cartridge 345 by activation of moving mechanisms such as pulleys 335 and gears 330a-330c by processor 210 into an extended position as shown in FIG. 2D for receiving bio-fluid from a user. In one embodiment, the user may indicate to the processor 210 that they have provided the bio-fluid onto the testing substrate 350 by activating of the user input mechanism such as a button 336, or other input device, which may be a second user input mechanism. Once the user has provided bio-fluid onto the extended substrate 350, the processor may cause the testing substrate 350 to be repositioned, e.g., moved back towards the cartridge 345, proximate the one or more BF constituent sensors 316 for processing and analyzing the bio-fluid. The one or more BF constituent sensors 316 may read more than one test results simultaneously, or may be read in sequence. This may depend on whether there are more than one optical sensors configured as part of the one or more BF constituent sensors 316. Moreover, the amount of time required to read a particular cell may determine if more than one cell can be read simultaneously, as different tests may take different processing times. In one embodiment, if read in sequence or serially, the testing substrate 350 may be moved more than once to reposition a test cell under the appropriate sensor. Once the processing has completed, the used testing substrate 350 may be disposed automatically in the toilet. The testing substrate 350 may be biodegradable. In this manner, the user is not required to touch any testing substrate at any time. In this manner, the bio-fluid collection apparatus 10 is self-cleaning.

Figure 2E:
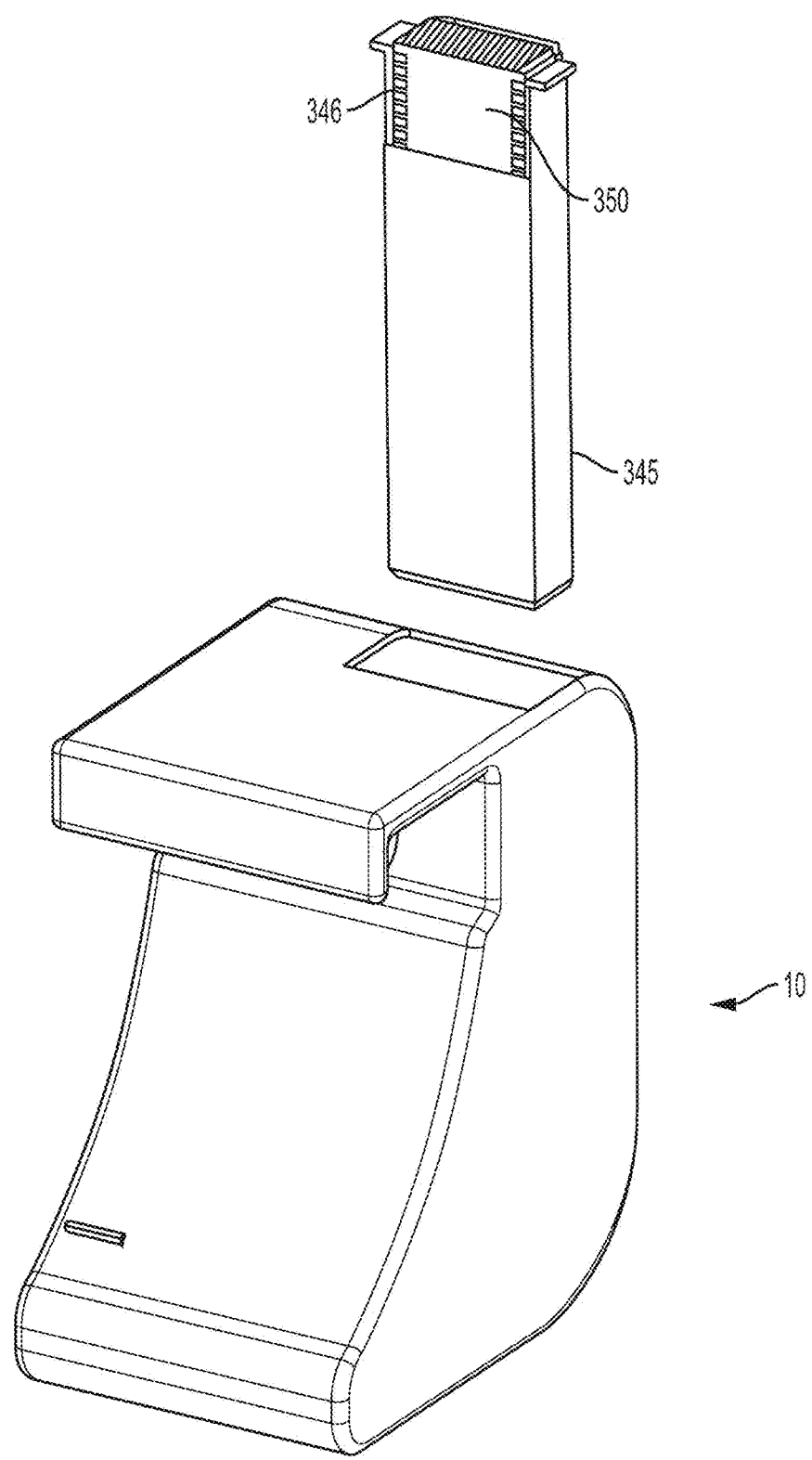
FIG. 2E is an illustration of the bio-fluid collection apparatus of FIG. 2C, but showing the replaceable cartridge 345 being inserted/removed.

FIG. 2E is an illustration of the bio-fluid collection apparatus of FIG. 2C, but showing the replaceable cartridge 345 being inserted/removed. The one or more testing substrates 350 may include perforations along the outer edges for being accessed by teeth of one or more gears 330a-330c. The one or more testing substrates 350 may be specific to a user and their needs, and each may have more than one testing cell, each being for a different test. The one or more testing substrates 350 may be prescribed according to the user's testing needs for testing for one or more conditions, unique constituent or property, as shown in relation to TABLE 1. Therefore, a user may have multiple conditions being tested for during one test session. The one or more testing substrates 350 or the cartridge 345 may be encoded to provide information to the processor 210 conveying which types of testing substrates 350, and combinations of test cells, are loaded so that proper processing can be achieved by the processor.

Figure 2F:
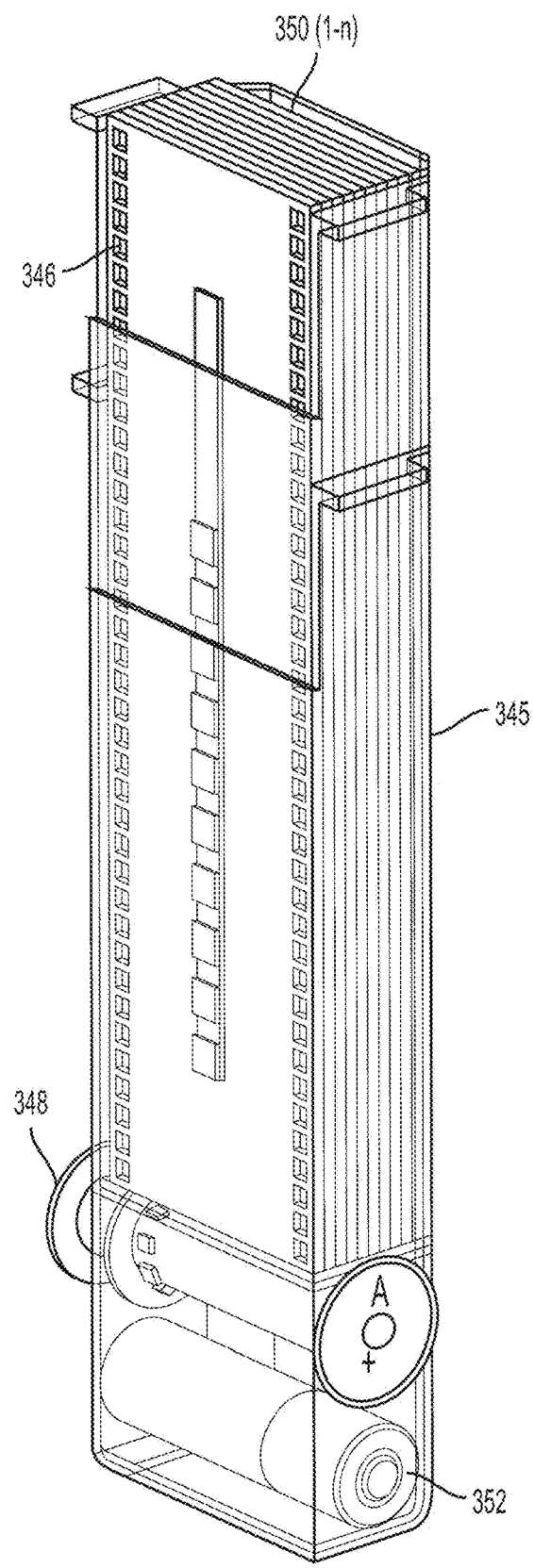
FIG. 2F is an illustration of an embodiment of a cartridge, according to principles of the disclosure.

FIG. 2F is an illustration of an embodiment of a cartridge, according to principles of the disclosure. The cartridge 345 is shown with one or more testing substrates 350 (1-n). In embodiments, the testing substrates may be individual singular strips, or may be multiple strips continuously attached in an accordion fashion, to be separated and disposed of when a user has completed a test process. In this embodiment, the cartridge 345 may be configured with moving mechanisms such as gears 348, instead of or in addition to those in the BF collection apparatus 10. The moving mechanisms such as gears 348 may propel the one or more testing substrates 350 into the BF collection apparatus 10, as needed, and may be under control of processor 210. In embodiments, as shown in FIG. 2F, a power source, such as battery 352, may be contained in the cartridge 345 to power components and operations of the BF collection apparatus 10. The battery 352 may be replaceable or rechargeable. The battery 352 may be charged wirelessly such as by capacitive or inductive coupling.

Figure 3:
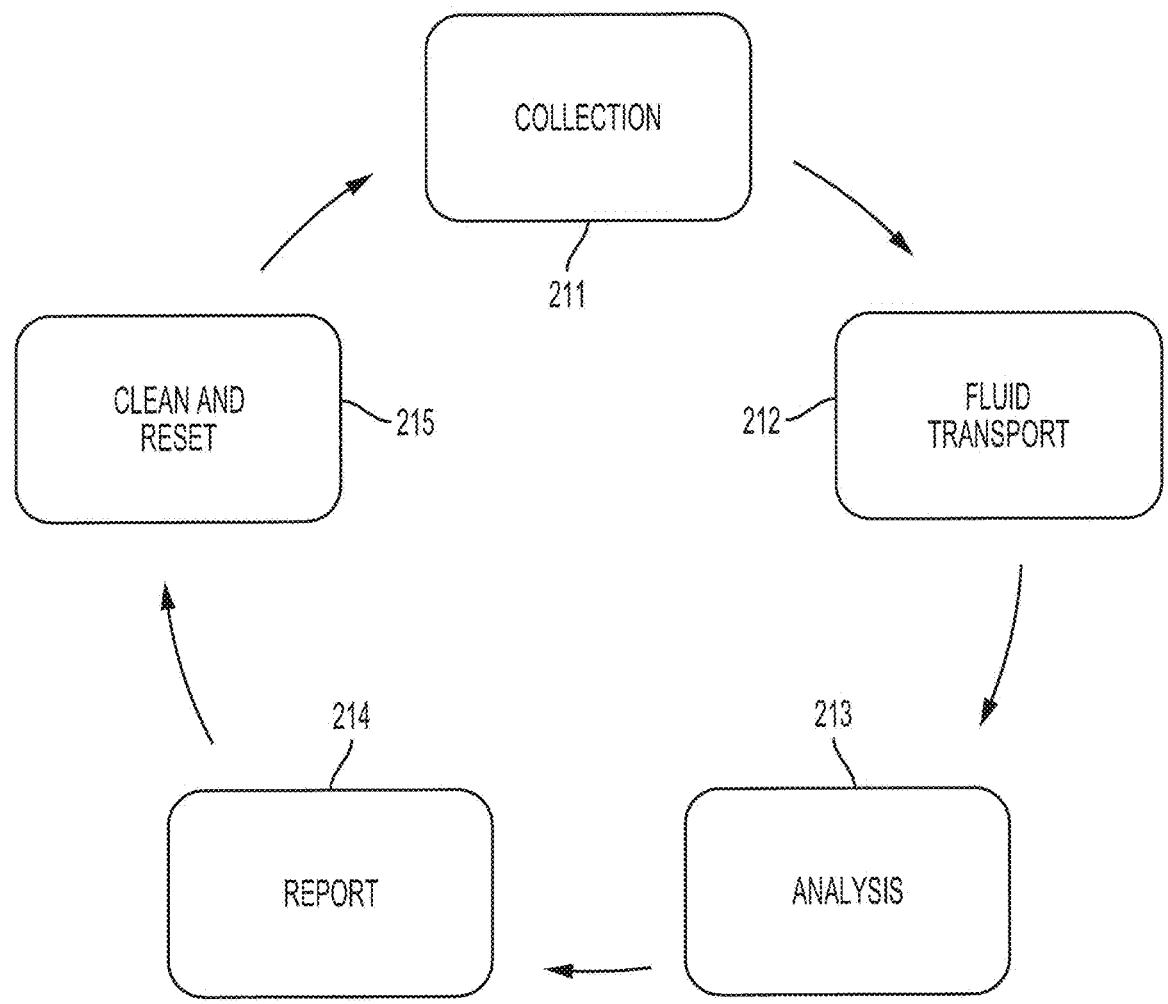
FIG. 3 shows a block diagram of an example of a method that may be implemented with the BFA system of FIG. 1.

FIG. 3 shows a block diagram of an example of a method of analyzing a bio-fluid sample via the BFA system 100, including the bio-fluid collection apparatus 10 of FIGS. 2C and 2D. Referring to FIGS. 1 and 3 contemporaneously, after a user initiates the BFA process using the user device 40 (such as, for example, an app that sends instruction and/or data signals to the BF collection apparatus 10 and/or BF analysis apparatus 20), a bio-fluid (BF) sample may be received at and collected by the BF collection apparatus 10 (Step 211). The collected sample may be transported to the BF analysis apparatus 20 (Step 212) and analyzed (Step 213). The results of the analysis carried out by the BF analysis apparatus 20 may be reported to the user device 40 and/or subscriber device 62 or a remote server (Step 214), after which the BF collection apparatus 10 may be automatically cleaned and reset (Step 215).

Figure 4:
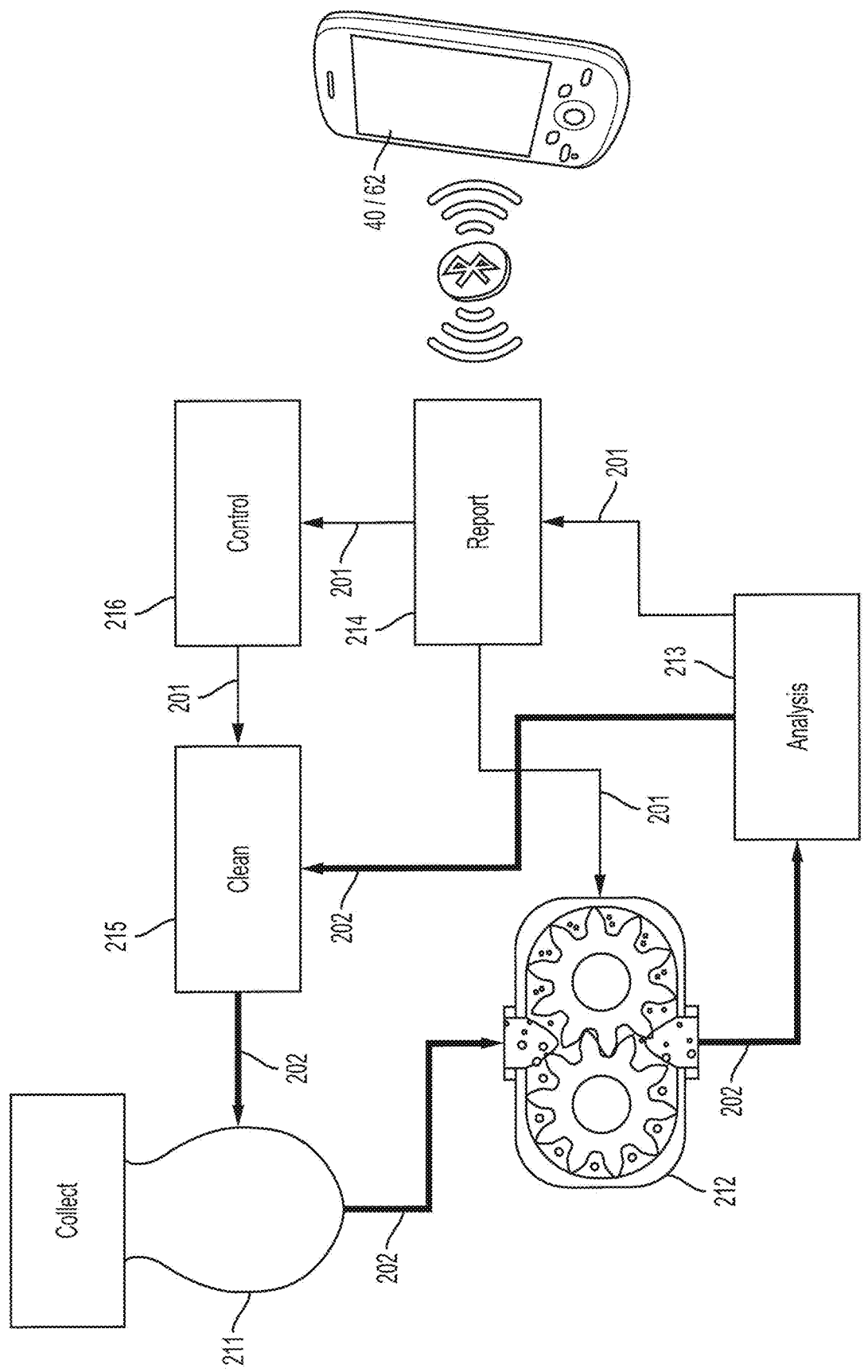
FIG. 4 shows a more detailed block diagram of the method of FIG. 3.

FIG. 4 shows a more detailed block diagram of the method of FIG. 3, including a control Step 216, electric signal channels 201, and BF fluid channels 202. In FIG. 4 the fluid transfer Step 212 is shown as being carried out by a pump, and the control Step 216 controls the cleaning mechanism in Step 215.

Referring back to FIG. 1, the testing device 24 may include a chemically activated monitoring substrate and/or a plurality of testing cells 326 (FIG. 2D), each of which may comprise a chemical that reacts with a BF constituent in the bio-fluid (e.g., urine) to give a qualitative test result, such as providing indications of conditions or constituents shown in TABLE 1. The analysis apparatus 20 may include a transmitter or transceiver 282 (transmitter and receiver) that communicates instruction and data signals with the user device 40, subscriber device 62, and/or the data storage and reporting system 50. The analysis apparatus 20 may receive BF constituent reference data from the data storage and reporting system 50. The BF analyzer 200 may compare concentrations or levels of one or more BF constituents in the bio-fluid with associated BF constituent reference data and output BF constituent analysis data based on the constituent concentration/levels of the one or more BF constituents in the bio-fluid. The analysis apparatus 20 may output the constituent analysis data to the reporting apparatus 70 (shown in FIG. 5). The BF analyzer 200 may compare values or levels of one or more BF properties of the bio-fluid with associated BF property reference data and output BF property analysis data based on the BF property values/levels of the one or more BF properties of the bio-fluid. The analysis apparatus 20 may output the BF property analysis data to the reporting apparatus 70 (shown in FIG. 5).

Figure 5:
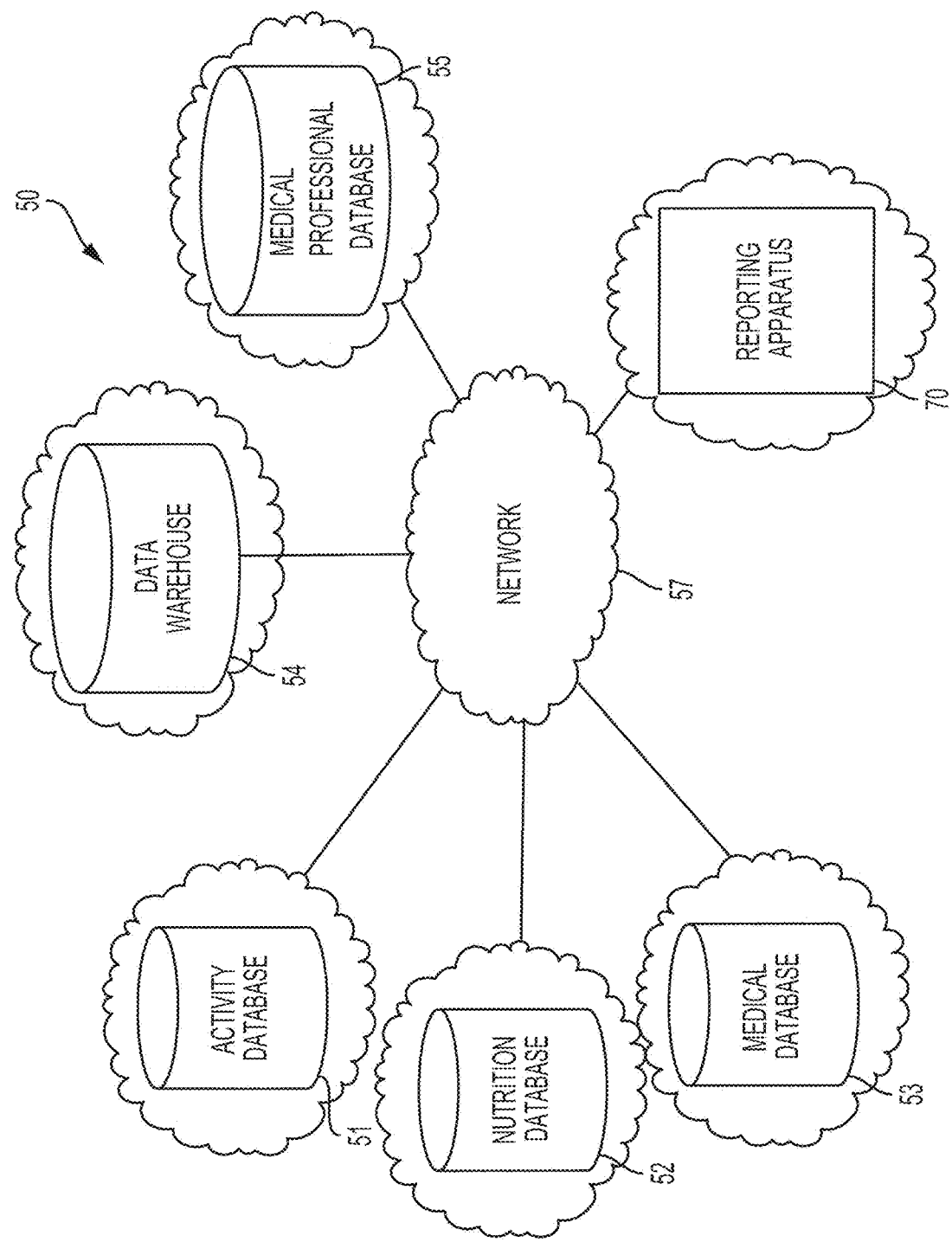
FIG. 5 shows an example of a data storage and reporting system that may be included in the BFA system of FIG. 1.

FIG. 5 shows an example of the data storage and reporting (DSR) system 50 (shown in FIG. 1). The DSR system 50 may include an activity database 51, a nutrition database 52, a medical database 53, a data warehouse 54, and a medical professional database 55 that contain the professional standards by which the results of the tests are compared or evaluated related to drugs, disease, pregnancy, conditions, and the like; any or all of which may be communicatively connected via a network 57, and may be connected to the BF collection apparatus 10. As seen in FIG. 5, any one or more of the databases 51-55 may be provided as a standalone database, or a database cloud (i.e., a plurality of databases configured as a cloud). The databases 51-55 may also illustratively represent at least one associated server. The DSR system 50 may further include the reporting apparatus 70, which may be provided as a standalone computer or server, or a cloud of computers or servers.

The DSR system 50 may receive, store, manage, and output BF constituent reference (or baseline) data, BF property reference (or baseline) data, user data, healthcare provider data, and the like. The data storage system may provide BF constituent reference data and/or BF property reference data for ongoing monitoring by the analysis apparatus 20. The BF constituent reference data, BF property reference data, user data, healthcare provider data, and/or the like, may be communicated securely between the DSR system 50 and analysis apparatus 20, user device 40, and/or subscriber device 62 over one or more secure communication channels. The data may be encrypted. The data may comprise user data, bio-fluid test/analysis data, BF constituent reference data, BF property reference data, and the like.

The user data may comprise user identification data, diet data, medication data, lifestyle data, vital statistics data, and/or the like. The user identification data may include, for example, name, identification number, social security number, account number, phone number, email address, mailing address, or any other identifier that may associate the user with the bio-fluid. The data may be communicated for immediate use, and include the user's background, diet, medications, and/or the like. The data may be made available in real-time to subscriber devices 62 and/or the user device 40.

Using the subscriber device 62, for example, healthcare providers such as hospital emergency rooms (ERs), urgent care professionals, personal doctors, and the like, may receive real-time BF test/analysis data, including, for example, urinalysis data. The data (including, for example, test results) can be confirmed or used in collaboration with other testing/analysis methodologies such as, a blood test, examination data, and/or other testing protocols.

In the DSR system 50, the activity database 51 may include up-to-date activity-related data, including data related to activities such as exercise, smoking, age, gender, weight, and the like. The activity-related data may be populated from publicly available databases such as those of the Center for Disease Control (CDC), National Institute for Health (NIH), and the like. The stored activity-related data may include base line data that correlates certain activities with BF constituents and/or BF properties of the bio-fluid analyzed in the BFA system 100.

The nutrition database 52, medical database 53, and medical professional database 55, similarly may be populated with the most current data relating to nutrition, medications, and diagnoses, respectively, pulled from related, publicly available databases. The stored nutrition, medical, and diagnostic data may include base line data and methodologies that correlate dietary nutrition, medication, and state-of-the art diagnostic data with BF constituents and/or BF properties of the bio-fluid analyzed in the BFA system 100.

The data warehouse 54 may store user data, subscriber data, historical BF constituent data for each user, historical BF property data for each user, and the like.

Referring back to FIG. 1, the BFA system 100 one or more BF constituents and one or more BF properties may be tested/analyzed (using, for example, a testing substrate 350 of FIG. 2D), and reporting data generated that identifies the specific BF constituents/properties, as well as the concentrations or levels of those BF constituents/properties in the sample. Raw data results may be communicated to the user device 40 and/or subscriber device 62. An application on the user device 40 may then cause the raw data to be uploaded to a data warehouse 54 (shown in FIG. 5) for subsequent mining and diagnostics.

Figure 6:
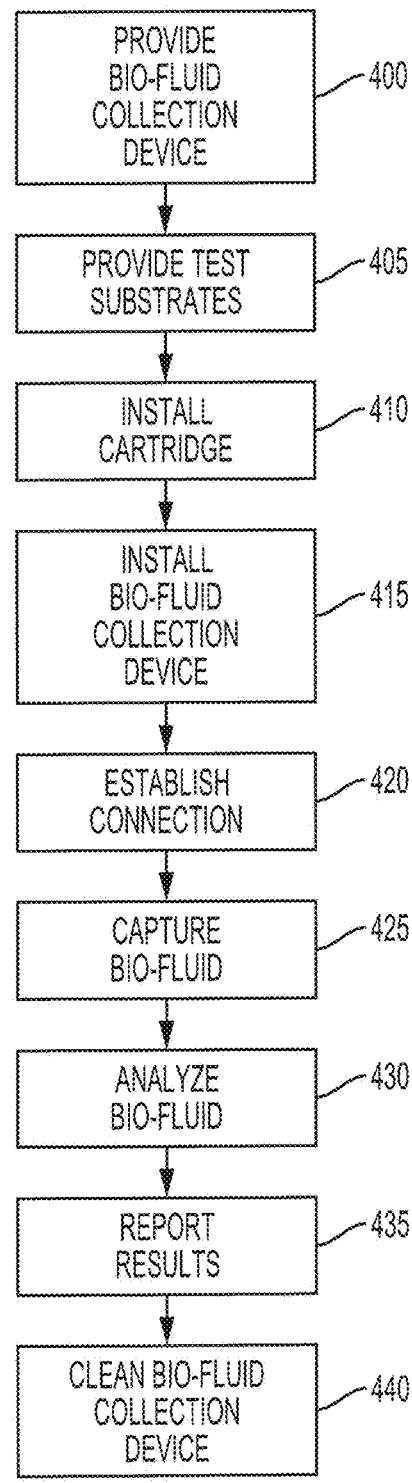
FIG. 6 is an example flow diagram for using the BFA system, the process performed according to principles of the disclosure.

FIG. 6 is an example flow diagram for using the BFA system 100, according to principles of the disclosure. The steps of the flow diagram may also represent a block diagram of components configured to perform certain of the related steps. The steps may comprise a computer program product that includes software instructions embodied on a computer-readable medium that when read and executed by a computer processor performs the respective step. At step 400, a bio-fluid collection device, such as bio-fluid collection apparatus 10, may be provided to a user for one-time use or ongoing use by the user to have one or more constituents measured or monitored in a bio-fluid. At step 405, at least one test substrate may be provided to the user. The at least one test substrate may comprise a plurality of test substrates such as substrate 350. This may be in the form of a cartridge 345, as described previously, for use with bio-fluid collection apparatus 10, and may include a plurality of test substrates. At step 410, the cartridge 345 may be installed in the bio-fluid collection apparatus 10. At step 415, the bio-fluid collection apparatus 10 may be installed on a toilet. Steps 410 may be performed before or after step 415. At step 420, a communication connection may be established from the bio-fluid collection apparatus 10 over a network 30, 57 for communicating with, e.g., a remote server, subscriber device 40, 62, database 51-54 and/or reporting apparatus 70. At step 425, bio-fluid may be captured for analysis, e.g., at the toilet, using bio-fluid collection apparatus 10. At step 430, the captured bio-fluid may be analyzed. At step 435, the results of the analysis may be reported, e.g., over a network 30, 57 for communicating with a remote server, subscriber device 40, 62, database 51-54 and/or reporting apparatus 70. At step 440, the bio-fluid collection apparatus 10 may be cleaned for a subsequent use, which may not require any cleaning action by the user.

A "computer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a central processing unit, a general purpose computer, a super computer, a personal computer, a laptop computer, a palmtop computer, a notebook computer, a desktop computer, a workstation computer, a server, or the like, or an array of processors, microprocessors, central processing units, general purpose computers, super computers, personal computers, laptop computers, palmtop computers, notebook computers, desktop computers, workstation computers, servers, or the like.

A "server," as used in this disclosure, means any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

A "database," as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communication(s) link," as used in this disclosure, means a wired and/or wireless medium that conveys data or information between at least two points. The wired or wireless medium may include, for example, a metallic conductor link, a radio frequency (RF) communication link, an Infrared (IR) communication link, an optical communication link, or the like, without limitation. The RF communication link may include, for example, WiFi, WiMAX, IEEE 802.11, DECT, 0G, 1G, 2G, 3G, 4G or 5G cellular standards, Bluetooth, or the like. A communication(s) link may include a public switched telephone network (PSTN) line, a voice-over-Internet-Protocol (VoIP) line, a cellular network link, an Internet protocol link, or the like. The Internet protocol may include an application layer (e.g., BGP, DHCP, DNS, FTP, HTTP, IMAP, LDAP, MGCP, NNTP, NTP, POP, ONC/RPC, RTP, RTSP, RIP, SIP, SMTP, SNMP, SSH, Telnet, TLS/SSL, XMPP, or the like), a transport layer (e.g., TCP, UDP, DCCP, SCTP, RSVP, or the like), an Internet layer (e.g., IPv4, IPv6, ICMP, ICMPv6, ECN, IGMP, IPsec, or the like), and a link layer (e.g., ARP, NDP, OSPF, Tunnels (L2TP), PPP, MAC (Ethernet, DSL, ISDN, FDDI, or the like), or the like).

A "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, the Internet, or the like, or any combination of the foregoing, any of which may be configured to communicate data via a wireless and/or a wired communication medium. These networks may run a variety of protocols not limited to TCP/IP, IRC or HTTP.

The terms "including," "comprising" and variations thereof, as used in this disclosure, mean "including, but not limited to," unless expressly specified otherwise. The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

A "computer-readable medium," as used in this disclosure, means any medium that participates in providing data (for example, instructions) which may be read by a computer. Computer-readable medium may be non-transitory, and not including transmission waves. Such a medium may take many forms, including non-volatile media, volatile media, and transmission media. Non-volatile media may include, for example, optical or magnetic disks and other persistent memory. Volatile media may include dynamic random access memory (DRAM). Transmission media may include coaxial cables, copper wire and fiber optics, including the wires that comprise a system bus coupled to the processor. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read. The computer-readable medium may include a "Cloud," which includes a distribution of files across multiple (e.g., thousands of) memory caches on multiple (e.g., thousands of) computers.

Various forms of computer readable media may be involved in carrying sequences of instructions to a computer. For example, sequences of instruction (i) may be delivered from a RAM to a processor, (ii) may be carried over a wireless transmission medium, and/or (iii) may be formatted according to numerous formats, standards or protocols, including, for example, WiFi, WiMAX, IEEE 802.11, DECT, 0G, 1G, 2G, 3G or 4G cellular standards, Bluetooth, or the like.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications, or modifications of the disclosure.

What is claimed is:

1. A bio-fluid analysis system comprising:
a first apparatus configured to be attached to a toilet and configured to capture bio-fluid from a user;
a second apparatus to analyze the bio-fluid and to determine one or more constituents in the bio-fluid, wherein the second apparatus includes a portion that forms a lip for attaching the second apparatus to a rim of a toilet bowl and the second apparatus projects one or more test substrates through the lip into the toilet bowl for receiving the bio-fluid thereon;
a first device that separates the captured bio-fluid from the first apparatus into separate channels for analysis by the second apparatus; and a mechanism to transmit results of an analysis of the captured bio-fluid by the second apparatus to a remote computer over a network.

2. The bio-fluid analysis system of claim 1, further comprising a compartment in a housing of the first apparatus to receive a cartridge containing one or more testing substrates for receiving the bio-fluid to be analyzed by the second apparatus.

3. The bio-fluid analysis system of claim 2, wherein each testing substrate includes a plurality of test cells, each cell for testing for at least one constituent in the bio-fluid.

4. The bio-fluid analysis system of claim 2, wherein each testing substrate includes a plurality of test cells each for testing for a level of one or more constituents in the bio-fluid.

5. The bio-fluid analysis system of claim 2, wherein the one or more constituents in the bio-fluid include one or more of: a pH value, a protein, a ketone, a sugar, a nitrite, leukocyte esterase, bilirubin, urobilinogen, red blood cells, white blood cells, calcium, amphetamine, barbiturates, benzodiazepines, buprenorphine, cocaine, cotinine, ecstasy (MDMA), ethyl alcohol, ethyl glucuronide, euphorics, fentanyl, heroin, hydrododone, LSD, marijuana, metabolite, methadone, methamphetamine, methaqualone, an opiate/Opoid, oxycodone, phencyclidine, phenobarbital, propoxyphene, a steroid, testable markers, synthetic cannabinoid, and THC cannabinoid.

6. The bio-fluid analysis system of claim 1, wherein the first apparatus includes a processor that is configured to control presenting one or more testing substrates over a lip portion of the toilet for receiving the bio-fluid to be analyzed by the second apparatus.

7. The bio-fluid analysis system of claim 1, wherein the second apparatus includes at least one optical sensor to determine a level of the one or more constituents in the bio-fluid.

8. The bio-fluid analysis system of claim 7, wherein the at least one optical sensor comprises a plurality of optical sensors.

9. The bio-fluid analysis system of claim 1, wherein the first apparatus includes a biodegradable test strip having thereon a plurality of test cells, each cell for testing for at least one different constituent in the bio-fluid.

10. The bio-fluid analysis system of claim 1, further comprising:
a cartridge containing one or more testing substrates for receiving the bio-fluid to be analyzed by the second apparatus; and
a compartment in a housing of the first apparatus to receive the cartridge, the cartridge containing a power source or a moving mechanism to move the one or more testing substrates proximate the second apparatus.

11. The bio-fluid analysis system of claim 10, wherein each of the one or more testing substrates comprises one or more test cells for testing for a level of one or more different constituents in the bio-fluid.

12. The bio-fluid analysis system of claim 1, wherein the first apparatus comprises at least one testing substrate for receiving the bio-fluid to be analyzed by the second apparatus, the at least one testing substrate includes a plurality of test cells, each cell for testing for a level of one or more different constituents in the bio-fluid.

13. The bio-fluid analysis system of claim 1, wherein the mechanism to transmit communicates results of the analysis to a server over the network for data storage and reporting.

14. The bio-fluid analysis system of claim 1, wherein the transmitted results are stored in a database of the bio-fluid analysis system and viewable by a healthcare professional.

15. The bio-fluid analysis system of claim 1, wherein the second apparatus further comprises a housing with two opposing sides including a front side and a rear side, the front side having a concave contour to align with a corresponding contour of an outer surface of a toilet bowl.

16. A bio-fluid analysis system comprising:
a first apparatus configured to be attached to a toilet and configured to capture bio-fluid from a user;
a second apparatus to analyze the bio-fluid and to determine one or more constituents in the bio-fluid, wherein the second apparatus includes a portion that forms a lip for attaching the second apparatus to a rim of a toilet bowl, wherein the second apparatus includes a portion that forms a lip for attaching the second apparatus to a rim of a toilet bowl and the second apparatus comprises a housing with two opposing sides including a front side and a rear side, the front side having a concave contour to align with a corresponding contour of an outer surface of a toilet bowl;
a first device that separates the captured bio-fluid from the first apparatus into separate channels for analysis by the second apparatus; and
a mechanism to transmit results of an analysis of the captured bio-fluid by the second apparatus to a remote computer over a network.

17. The bio-fluid analysis system of claim 16, wherein the second apparatus projects one or more test substrates through the lip into the toilet bowl for receiving the bio-fluid thereon.

* * * * *